US012773160B2

(12) United States Patent
Fraga Da Silva et al.

(10) Patent No.: US 12,773,160 B2
(45) Date of Patent: Oct. 27, 2026

(54) TUMESCENCE MONITORING SYSTEM FOR DIAGNOSING ERECTILE DYSFUNCTION AND METHODS OF USE

(71) Applicant: ECOLE POLYTECHNIQUE FEDERALE DE LAUSANNE (EPFL), Lausanne (CH)

(72) Inventors: Rodrigo Araujo Fraga Da Silva, Saint-Sulpice (CH); Nikolaos Stergiopulos, Preverenges (CH); Chris Steven Braissant, Oron-la-Ville (CH)

(73) Assignee: Ecole Polytechnique Federale De Lausanne (EPFL), Lausanne (CH)

( * ) Notice: Subject to any disclaimer, the term of this patent is extended or adjusted under 35 U.S.C. 154(b) by 781 days.

(21) Appl. No.: 18/193,532

(22) Filed: Mar. 30, 2023

(65) Prior Publication Data

US 2023/0309910 A1 Oct. 5, 2023

Related U.S. Application Data

(60) Provisional application No. 63/362,362, filed on Apr. 1, 2022.

(51) Int. Cl.
*A61B 5/00* (2006.01)
*A61N 1/36* (2006.01)

(52) U.S. Cl.
CPC .......... *A61B 5/4393* (2013.01); *A61B 5/0022* (2013.01); *A61B 5/6813* (2013.01); *A61N 1/36007* (2013.01)

(58) Field of Classification Search
CPC .................................................... A61B 5/4393
See application file for complete search history.

(56) References Cited

U.S. PATENT DOCUMENTS 3,941,136 A 3/1976 Bucalo
4,515,166 A 5/1985 Timm
(Continued)

FOREIGN PATENT DOCUMENTS

CN 105011939 A * 11/2015
CN 110710959 A * 1/2020 .......... A61B 5/1077
(Continued)

OTHER PUBLICATIONS

Alsaid, et al., coexistence of adrenergic and cholinergic nerves in the inferior hypogastric plexus: anatomical and immunohistochemical study with 3D reconstruction in human male fetus, J. Anat., 214(5):645-654 (2009).
(Continued)

*Primary Examiner* — Thaddeus B Cox
(74) *Attorney, Agent, or Firm* — Greenberg Traurig, LLP; Christopher C. Bolten; Albert K Heng

(57) ABSTRACT

Systems and methods for monitoring penile tumescence are provided that overcome the drawbacks of previously known systems by providing a wearable formed of a flexible and elastic tube having a plurality of sensors disposed on or embedded within it, the wearable configured to be applied to a penis of a subject, and a spaced-apart controller operatively coupled to retrieve data regarding circumferential and axial dimensional changes and penile rigidity from the plurality of sensors and transmit that data to an external computer or smartphone for analysis and display. The plurality of sensors may be coupled to the spaced-apart controller via a flexible lead or wirelessly using a passive RFID system.

18 Claims, 4 Drawing Sheets

(56) References Cited

U.S. PATENT DOCUMENTS

| | | | | | |
|---|---|---|---|---|---|
| 4,585,005 | A | | 4/1986 | Lue et al. | |
| 4,913,162 | A | * | 4/1990 | Leang | A61B 5/4393 600/587 |
| 5,215,088 | A | | 6/1993 | Normann et al. | |
| 5,454,840 | A | | 10/1995 | Krakovsky et al. | |
| 5,938,584 | A | | 8/1999 | Ardito et al. | |
| 6,015,393 | A | * | 1/2000 | Hovland | A61B 5/0535 600/587 |
| 6,128,536 | A | | 10/2000 | Noack et al. | |
| 6,162,188 | A | * | 12/2000 | Barnea | A61B 5/4393 600/587 |
| 6,169,924 | B1 | | 1/2001 | Meloy et al. | |
| 6,259,945 | B1 | | 7/2001 | Epstein et al. | |
| 6,505,074 | B2 | | 1/2003 | Boveja et al. | |
| 6,650,943 | B1 | | 11/2003 | Whitehurst et al. | |
| 6,885,895 | B1 | | 4/2005 | Whitehurst et al. | |
| 6,993,390 | B2 | | 1/2006 | Zappala | |
| 7,006,870 | B1 | | 2/2006 | Whitehurst et al. | |
| 7,096,070 | B1 | | 8/2006 | Jenkins et al. | |
| 7,328,068 | B2 | | 2/2008 | Spinelli et al. | |
| 7,328,069 | B2 | | 2/2008 | Gerber | |
| 7,330,762 | B2 | | 2/2008 | Boveja et al. | |
| 7,338,522 | B2 | | 3/2008 | Greenberg et al. | |
| 7,369,894 | B2 | | 5/2008 | Gerber | |
| 7,427,280 | B2 | | 9/2008 | Gerber | |
| 7,660,631 | B2 | | 2/2010 | Whitehurst et al. | |
| 7,734,355 | B2 | | 6/2010 | Cohen et al. | |
| 7,862,551 | B2 | | 1/2011 | Bates | |
| 7,865,243 | B1 | | 1/2011 | Whitehurst et al. | |
| 8,467,875 | B2 | | 6/2013 | Bennett et al. | |
| 8,630,711 | B1 | | 1/2014 | Wark et al. | |
| 9,247,904 | B2 | | 2/2016 | Hotaling | |
| 9,464,948 | B2 | | 10/2016 | Carroll et al. | |
| 9,821,163 | B2 | | 11/2017 | Fraga Da Silva et al. | |
| 10,232,175 | B2 | | 3/2019 | Possover | |
| 10,300,279 | B2 | | 5/2019 | Fraga et al. | |
| 11,141,589 | B1 | | 10/2021 | Fraga et al. | |
| 11,141,590 | B1 | | 10/2021 | Fraga Da Silva et al. | |
| 2003/0004553 | A1 | | 1/2003 | Grill et al. | |
| 2003/0236557 | A1 | | 12/2003 | Whitehurst et al. | |
| 2004/0049240 | A1 | | 3/2004 | Gerber et al. | |
| 2004/0073268 | A1 | | 4/2004 | Zappala | |
| 2004/0243205 | A1 | | 12/2004 | Keravel et al. | |
| 2005/0010260 | A1 | | 1/2005 | Gerber | |
| 2005/0113877 | A1 | | 5/2005 | Spinelli et al. | |
| 2005/0131484 | A1 | | 6/2005 | Boveja et al. | |
| 2005/0283202 | A1 | | 12/2005 | Gellman | |
| 2006/0129028 | A1 | | 6/2006 | Krakousky | |
| 2006/0135862 | A1 | | 6/2006 | Tootle et al. | |
| 2007/0027514 | A1 | | 2/2007 | Gerber | |
| 2007/0078493 | A1 | | 4/2007 | Gerber | |
| 2007/0255333 | A1 | | 11/2007 | Giftakis et al. | |
| 2008/0065167 | A1 | | 3/2008 | Boggs, II et al. | |
| 2008/0091244 | A1 | | 4/2008 | Richardson | |
| 2008/0140168 | A1 | | 6/2008 | Walter et al. | |
| 2010/0016759 | A1 | | 1/2010 | Lavoisier | |
| 2013/0123684 | A1 | | 5/2013 | Giuffrida et al. | |
| 2014/0277266 | A1 | | 9/2014 | Khalil et al. | |
| 2014/0304773 | A1 | | 10/2014 | Woods et al. | |
| 2014/0316484 | A1 | | 10/2014 | Edgerton et al. | |
| 2016/0101288 | A1 | | 4/2016 | Fraga Da Silva et al. | |
| 2017/0281945 | A1 | | 10/2017 | Gill et al. | |
| 2018/0043164 | A1 | | 2/2018 | Fraga Da Silva et al. | |
| 2021/0251562 | A1 | | 8/2021 | Jain et al. | |
| 2024/0091538 | A1 | | 3/2024 | Fraga Da Silva et al. | |
| 2024/0216691 | A1 | | 7/2024 | Fraga Da Silva et al. | |

FOREIGN PATENT DOCUMENTS

| | | | | | |
|---|---|---|---|---|---|
| CN | 212996394 | U | * | 4/2021 | |
| DE | 102019131530 | A1 | | 5/2021 | |
| KR | 20190115833 | A | * | 10/2019 | A61B 5/6813 |
| KR | 20200095839 | A | * | 8/2020 | A61B 5/6831 |
| WO | WO-9639932 | A1 | | 12/1996 | |
| WO | WO-03018113 | A1 | | 3/2003 | |
| WO | WO-2009023543 | A2 | | 2/2009 | |
| WO | WO-2013011474 | A2 | | 1/2013 | |
| WO | WO-2017209673 | A1 | | 12/2017 | |
| WO | WO-2021032879 | A1 | | 2/2021 | |
| WO | WO-2024180482 | A1 | | 9/2024 | |

OTHER PUBLICATIONS

Beretta, et al., Reproductive Aspect in Spinal Cord Injured Males, Paraplegia, 27(2):113-118 (Apr. 1989).

Brackett, et al., Treatment of infertility in men with spinal cord injury, Nat. Rev. Urol., 7(3):162-172 (Mar. 2010).

Burnett, et al., Intraoperative Assessment of an Implantable Electrode Array for Cavernous Nerve Stimulation, J. Sex Med., 5(8):1949-1954 (2008).

Burnett, et al., Neuromodulatory Therapy to Improve Erectile Function Recovery Outcomes After Pelvic Surgery, J. Urol., 176(3):882-887 (2006).

Clavell-Hernandez et al., Penile Rehabilitation Following Prostate Cancer Treatment: Review of Current Literature, Asian J. Andrology, 17:916-922 (Apr. 2015).

Costello, et al., Immunohistochemical Study of the Cavernous Nerves in the Periprostatic Region, BJU Int., 107(8):1210-1215 (2011).

Dean, et al., Physiology of Penile Erection and Pathophysiology of Erectile Dysfunction, Urol. Clin. North Am., 32(4):379-395 (2005).

Eardley, et al., Pharmacotherapy for Erectile Dysfunction, J. Sex. Med., 7:524-540 (2010).

Everaert, et al., Neuroanatomy and neurophysiology related to sexual dysfunction in male neurogenic patients with lesions to the spinal cord or peripheral nerves, Spinal Cor., 48(3):182-191 (Mar. 2010).

Fode et al., Penile rehabilitation after radical prostatectomy: what the evidence really says, BJU Int., 112(7):998-1008 (2013).

Gandaglia et al., Penile Rehabilitation After Radical Prostatectomy: Does it Work? Transl. Androl. Urol., 4(2):110-123 (Jan. 2015).

Gomes, et al., Erectile Dysfunction-Erectile Function Predicts Sexual Satisfaction in Men With Spinal Cord Injury, Sexual Medicine, 5(3):148-155 (Sep. 2017).

Harding, et al., Comparison of a Needle-Free High-Pressure Injection System with Needle-Tipped Injection of Intracavernosal Alprostadil for Erectile Dysfunction, Int. J. Impot. Res., 14(6):498-501 (2002).

Ibrahim, et al., Male fertility following spinal cord injury: an update, Andrology, 4(1):13-26 (Jan. 2016).

International Preliminary Report on Patentability dated Apr. 24, 2017 in Int'l PCT Patent Appl No. PCT/IB2015/057809, 8 pages.

International Search Report & Written Opinion dated Jun. 28, 2022 in Int'l PCT Patent Appl. Serial No. PCT/IB2022/051127.

International Search Report and Written Opinion dated Jan. 20, 2016 in Int'l PCT Patent Application Serial No. PCT/IB2015/057809.

Klotz, et al., Early Experience with Intraoperative Cavernous Nerve Stimulation with Penile Tumescence Monitoring to Improve Nerve Sparing During Radical Prostatectomy, Urology, 52(4):537-542 (1998).

Klotz, et al., Intraoperative Cavernous Nerve Stimulation During Nerve Sparing Radical Prostatectomy: How and When?, Curr. Opin. Urol., 10(3):239-43 (2000).

Leungwattanakij, et al., Intracavernosal Injection and Intraurethral Therapy for Erectile Dysfunction, Urol. Clin. North Am. 28(2):343-54 (2001).

Lue, et al., Electrostimulation and Penile Erection, Urol. Int., 40(1):60-64 (1985).

Lue, et al., Intraoperative Electrostimulation of the Cavernous Nerve: Technique, Results and Limitations, The Journal of Urology, 154:1426-1428 (1995).

Moreland, R.B., Is There a Role of Hypoxemia in Penile Fibrosis: a Viewpoint Presented to the Society for the Study of Impotence, Int'l. J Impotence Research, 10:113-120 (1998).

Mulhall et al., Standard Operating Procedure for the Preservation of Erectile Function Outcomes After Radical Prostatectomy, J Sex Med., 10(1):195-203 (2013).

(56) References Cited

OTHER PUBLICATIONS

Muller et al., The Effect of Hyperbaric Oxygen Therapy on Erectile Function Recovery in a Rat Cavernous Nerve Injury Model, J Sex Med., 5(3):562-570 (2008).
O'Kelly, et al., Electroejaculatory Stimulation and Its Implications for Male Infertility in Spinal Cord Injury: a Short History Through Four Decades of Sperm Retrieval 91975-2010), Urology, 77(6):1349-1352 (2011).
Penson et al., 5-Year Urinary and Sexual Outcomes After Radical Prostatectomy: Results From the Prostate Cancer Outcomes Study, J. Urol. 173:1701-1705 (May 2005).
Penson, et al., 5-Year Urinary and Sexual Outcomes after Radical Prostatectomy: Results from the Prostate Cancer Outcomes Study, J. Urol., 179 (5 Suppl): S40-44 (2008).
Perelman, et al., Evaluation and Treatment of The Ejaculatory Disorders, Atlas of Male Sex Dysfunction, pp. 127-157 (2004).
Ponnusamy, et al., Nerve Mapping for Prostatectomies: Novel Technologies Under Development, J. Endourol., 26(7):769-77 (2012).
Rotella., Phosphodiesterase 5 inhibitors: Current Status and Potential Applications, Nat. Rev. Drug Discov., 1(9):674-682 (2002).
Sadeghi-Nejad., Penile Prosthesis Surgery: a Review of Prosthetic Devices and Associated Complications, J. Sex. Med., 4(4):1520 (2007).
Segal et al., Current Penile-Rehabilitation Strategies: Clinical Evidence, Arab J. Urol., 11:230-0236 (Mar. 2013).
Shafik, A., Extrapelvic Cavernous Nerve Stimulation in Erectile Dysfunction, Human study, Andrologia, 28(3):151-156 (1996).
Shafik, et al., Magnetic Stimulation of the Cavernous Nerve for the Treatment of Erectile Dysfunction in Humans, Int. J. Impot. Res., 12(3):137-141 (2000).
Shafik et al., Percutaneous Perineal Electrostimulation Induces Erection: Clinical Significance in Patients With Spinal Cord Injury and Erectile Dysfunction, The Journal of Spinal Cord Medicine, 31(1):40-43 (2008).
Skoufias et al., Novel Concept Enabling an Old idea: a Flexible Electrode Array to Treat Neurogenic Erectile Dysfunction, J Sex Med., 15:1558-1569 (Sep. 2018).
Takenaka, et al., Variation in Course of Cavernous Nerve with Special Reference to Details of Topographic Relationships Near Prostatic Apex: Histologic Study Using Male Cadavers, Urology, 65(1):136-142 (2005).
Trofimenko, et al., Fertility Treatment in spinal cord injury and other neurologic disease, Transl. Androl. Urol., 5(1):102-116 (Feb. 2016).
Wang, R., Penile Rehabilitation after Radical Prostatectomy: Where Do We Stand and Where Are We Going?, J Sex Med., 4:1085-1097 (2007).
Zhao, et al., 3D-printed highly stable flexible strain sensor based on silver-coated-glass fiber-filled conductive silicon rubber, Materials & Design, 193:108788 (Aug. 2020).
International Search Report & Written Opinion dated Jul. 13, 2023 in Int'l PCT Patent Appl. Serial No. PCT/IB2023/053215.
Costello, et al., Abstract of First in Man Pilot Study of Permanent Implant of a Cavernous Nerve Neurostimulator for Erectile Function Preservation, the Journal of Urology, 213, No. 5S2, Supplement, 2025.
Costello, et al., First in man study of cavernous nerve neurostimulator for erectile function preservation, BJU Int 2025 doi:10.1111/bju.70066 (Nov. 13, 2025) available at https://bjui-journals.onlinelibrary.wiley.com/doi/10.1111/bju.70066.
De Groat, et al., Afferent Nerve Regulation of Bladder Function in Health and Disease, Handb. Exp. Pharmacol., 194:91-138 (2009).
De Groat, et al., Neural Control of the Lower Urinary Tract, Compr. Physiol., 5(1):327-396 (Jan. 2015).
Dundee, et al., First-in-Human Implantable Neurostimulator for Erectile Function Rehabilitation Post-Prostatectomy: Early Results, Abstract Citation No. 023 from 25th World Meeting on Sexual Medicine, p. vi11 (Sep. 2024).
ElAbd, et al., Role of Electrical Stimulation in Peripheral Nerve Regeneration: a Systematic Review, Plastic and Reconstructive Surgery-Global Open, 10(3):e4115 (Mar. 2022).
Fowler, et al., The neural control of micturition, Nat. Rev. Neurosci., 9(6):453-466 (Jun. 2008).
Gordon, T., Brief Electrical Stimulation Promotes Recovery After Surgical Repair of Injured Peripheral Nerves, Int. J. Mol. Sci., 25(1):665 (Jan. 2024).
Haastert-Talini, et al., Electrical Stimulation Accelerates Axonal and Functional Peripheral Nerve Regeneration Across Long Gaps, Journal of Neurotrauma, 28:661-674 (Apr. 2011).
Liu, et al., The Role of Electrical Stimulation in Peripheral Nerve Regeneration: Current Evidence and Future Directions, Journal of Hand Surgery Global Online, 6:718-721 (2024).
Lu, et al., Use of Electrical Stimulation at Different Current Levels to Promote Recovery After Peripheral Nerve Injury in Rats, the Journal of TRAUMA Injury, Infection and Critical Care, 67(5):1066-1072 (Nov. 2009).
Park, et al., Effects of repeated 20 Hz electrical stimulation on functional recovery following peripheral nerve injury, Neurorehabil. Neural Repair, 33(9):775-784 (Sep. 2019).
Sayanagi, et al., Brief Electrical Stimulation Accelerates Axon Regeneration and Promotes Recovery Following Nerve Transection and Repair in Mice, J. Bone Joint Surg. Am., 103:880 (1-9) (2020).
Sharif, et al., Effectiveness of Functional Electrical Stimulation (FES) versus Conventional Electrical Stimulation in Gait Rehabilitation of Patients with Stroke, Journal of the College of Physicians and Surgeons Pakistan, 27(11):703-706 (2017).
Sturny, et al., Low-Intensity Electrostimulation Enhances Neuroregeneration and Improves Erectile Function in a Rat Model of Cavernous Nerve Injury, Journal of Sexual Medicine, 19(5):686-695 (May 2022).

* cited by examiner

TUMESCENCE MONITORING SYSTEM FOR DIAGNOSING ERECTILE DYSFUNCTION AND METHODS OF USE

CROSS-REFERENCE TO RELATED APPLICATIONS

This application claims priority to U.S. Provisional Patent Application No. 63/362,362, filed on Apr. 1, 2022, the entire contents of which are incorporated herein by reference.

FIELD OF THE INVENTION

The present invention relates generally to improved systems and methods for monitoring nocturnal penile tumescence, particularly for use in diagnosing erectile dysfunction, and may be especially advantageous for use in optimizing an implantable electrode array configured to improve erectile function.

BACKGROUND

A sexual disorder (e.g., sexual dysfunction, sexual malfunction) is a complication experienced by an individual, male or female, or a couple during any stage of normal sexual activity, including erection, physical pleasure, desire, preference, arousal, or orgasm. Sexual dysfunctions generally have a profound impact on an individual's quality of life. The most prevalent sexual disorders are erectile dysfunction (ED) and female sexual arousal disorders (FSAD).

Penile erection is a coordinated neurocardiovascular response. See, Dean R C and Lue T F, *Physiology of penile erection and pathophysiology of erectile dysfunction*, Urol Clin North Am. 2005 November; 32(4):379-95. In the flaccid state, the penile smooth muscles are tonically contracted, allowing only a small amount of blood flow for nutritional purposes. Penile erection occurs when sexual stimulation triggers release of neurotransmitters, mainly nitric oxide, from the cavernous nerve terminals. The neurotransmitters cause relaxation of the smooth muscle cells in cavernosal arterioles and sinuses, resulting in increased blood flow into the penis. This causes the cavernous sinuses to fill with blood and expand against the tunica albuginea, partially occluding the venous outflow, thus resulting in an erection.

ED is a multi-causal disease with diversified etiologies, and may be psychogenic, vasculogenic, hormonal, or neurogenic. It is generally believed that patients with purely psychogenic impotence achieve normal erections nocturnally. Patients with organic impotence, on the other hand, generally suffer impaired erectile performance both nocturnally and while awake, and accordingly, monitoring nocturnal penile tumescence is a known technique for distinguishing between impotence of psychogenic and organic origin.

Studies show that the neurogenic and vasculogenic causes are the most prevalent causes of ED. In general, the major mechanisms responsible for ED are a failure in the neuronal response (e.g., prostatectomy, cystectomy, abdominoperineal resection, spinal cord injury, or diabetes) or an increase in the tone and/or contractility of the smooth muscle within the corpus cavernosum and penile arteries (e.g., hypertension, atherosclerosis and diabetes). See, Sadeghi-Nejad H., *Penile prosthesis surgery: a review of prosthetic devices and associated complications*, Sex Med. 2007 March; 4(2):296-309.

Prostatectomy is known to cause severe ED. This essential surgical procedure, generally for treatment of prostate cancer, often leads to ED due to disruption of the neural pathway for erectile function. In particular, the intimal nerves are located around the prostate, and may be damaged during the surgery. Currently, surgeons attempt to perform a nerve-sparing surgery; nonetheless, an astounding 70% of patients undergoing prostatectomy will develop ED. See. Penson D F, McLerran D, Feng Z, Li L, Albertsen P C, Gilliland F D, Hamilton A. Hoffman R M, Stephenson R A, Potosky A L, Stanford J L., 5-*year urinary and sexual outcomes after radical prostalectomy: results from the Prostate Cancer Outcomes Study*, J Urol. 2008 May; 179(5 Suppl): S40-4.

Pharmacological treatments are currently available for ED. These drugs (e.g., sildenafil, Viagra®; tadalafil, Cialis® or vardenafil. Levitra®) are efficient for the majority of ED patients; however, they show low effectiveness for ED resulting from prostatectomy or others causes associated with failure in the neuronal response. Such drugs act by potentiating the actions of the neurotransmitter nitric oxide, by inhibiting the enzyme phosphodiesterase type 5 IPDE-5). See, Rotella D P., *Phosphodiesterase* 5 *inhibitors: current status and potential applications*, Nat Rev Drug Discov. 2002 September; 1(9):674-82. PDE-5 is an enzyme responsible for breaking down the intracellular second messenger cGMP generated by NO stimulus. cGMP is involved in the regulation of some protein-dependent kinases, which relax smooth muscle cells and facilitate erection. Thus, patients with disruption of the erectile neural response do not respond well to such medications. One alternative for these patients is intrapenial injections of vasodilators, which produce direct erection, independent of the neural pathway. See. Leungwattanakij S, Flynn V Jr, Hellstrom W J, *Intracavernosal injection and intraurethral therapy for erectile dysfunction*, Urol Clin North Am. 2001 May; 28(2):343-54 and Harding L M, Adeniyi A, Everson R, Barker S. Ralph D J, Baranowski A P, *Comparison of a needle-free high-pressure injection system with needle-tipped injection of intracavernosal alprostadil for erectile dysfunction*, Int J Impot Res. 2002 December; 14(6):498-501. Alprostadil (Prostaglandin E1, PGE1) is the most common vasodilator used for ED. See. Harding and Eardley I, Donatucci C, Corbin J, El-Meliegy A. Hatzimouratidis K, McVary K, Munarriz R, Lee S W, *Pharmacotherapy for erectile dysfunction*, J Sex Med. 2010 January; 7(1 Pt 2):524-40. The vasodilator may be injected into the corpus cavernosum with a needle and is effective in over 80% of patients. See. Harding. Common side effects of intrapenial injection are penile pain, bleeding, hematoma, priapism, and penile fibrosis, which can lead to permanent ED. See, Leungwattanakij.

Another option for these patients is penile implants, which consist of a pair of malleable or inflatable rods surgically implanted within the erection chambers of the penis. See, Sadeghi-Nejad. There are different types of penile prosthesis (rigid, semi-rigid, or inflatable) and all of those prostheses normally require an irreversible and destructive surgery with risk of intra and post-operative complications. Such prostheses frequently require surgical revision. Nevertheless, prosthesis implantation is a common procedure due to the lack of better treatment options. Thus, there is a clear need for better therapeutic strategy for the treatment of ED resulting from failure of the neural pathway, such as post-prostatectomy ED, providing a painless, safe, easier, non-traumatic and more effective alternative.

Numerous studies have shown that cavernous nerve stimulation can induce and maintain erection in animals and men. See, Lue T F, Schmidt R A, Tanagho E A, *Electrostimulation and penile erection*, Urol Int. 1985; 40(1):60-4;

Shafik A, Shafik A A, Shafik I A, El Sibai 0., *Percutaneous perinea! electrostimulation induces erection: clinical significance in patients with spinal cord injury and erectile dysfunction*. J Spinal Cord Med. 2008; 31(1):40-3; and Shafik A, el-Sibai 0, Shafik A A, *Magnetic stimulation of the cavernous nerve for the treatment of erectile dysfunction in humans*, Int J Impot Res. 2000 June; 12(3):137-41. Since then, electroneurostimulation for erectile response has been considered an option for patients undergoing prostatectomy. The barrier for the development of such technology, however, is the complex anatomy of the human cavernous nerve. See, Klotz L., *Intraoperative cavernous nerve stimulation during nerve sparing radical prostatectomy: how and when*? Curr Opin Urol. 2000 May; 10(3):239-43 and Ponnusamy K, Sorger J M, Mohr C., *Nerve mapping for prostatectomies: novel technologies under development*, J Endourol. 2012 July; 26(7):769-77. Locating the optimal site for electroneurostimulation is difficult, as the human cavernous nerve travels from the pelvic-plexus to the penis through a complex anastomosis. Moreover, there is significant anatomic variability in the location of the cavernous nerve; the pelvic-plexus is a diaphanous veil with microscopic nerves and the cavernous nerve is not disposed uniformly in every man. Further, each patient's anatomy, disease stage, and cancer location are unique. Collectively, these barriers make the identification of the cavernosal nerve segments for selective stimulation extremely difficult.

In some previously known systems, localization and identification of the cavernosal nerve is conducted during implantation surgery. For example, U.S. Pat. No. 4,585,005 to Lue requires previous identification and isolation of the cavernous nerves. U.S. Pat. No. 7,328,068 to Spinelli describes a method for stimulation of the penile neural pathway that requires precise positioning of the implant to achieve optimal stimulation. In Spinelli, a neurophysiological monitoring assessment could be used as method to locate the optimal stimulation site before implantation. U.S. Pat. No. 7,330,762 to Boveja discloses systems for electroneurostimulation of the cavernosal nerve, including different types of electrodes, such as spiral electrodes, cuff electrodes, steroid eluting electrodes, wrap-around electrodes and hydrogel electrodes. Again, the Boveja system requires identification of the optimal site for stimulation before implantation. U.S. Pat. No. 7,865,243 to Whitehurst describes systems and methods for stimulation of the cavernosal nerve; however, the anatomical identification of the course of the pudendal nerve and/or other nerves to be stimulated must be located before implantation.

Recently, significant gains have been made in achieving practical neuroelectrostimulation systems for treatment of ED that enable localization and identification of the cavernous nerve post implantation. For example, U.S. Pat. Nos. 9,821,163 and 10,300,279 to Fraga da Silva et al., invented by the inventors of the present application, describes neuroelectrostimulation systems wherein electrodes are stimulated post-implantation to empirically determine a preferred electrode excitation configuration to achieve sexual arousal. While the inventions described in those patents represent a significant advance in the use of neuroelectrostimulation to treat ED, it would be desirable to provide methods for reliably determining an electrode excitation configuration for creating arousal in which the electrode excitation configuration can be determined by an automated process.

After bilateral nerve-sparing radical prostatectomy, some patients may recover from erectile dysfunction, especially younger patients without a history or associated-risk factors for ED. However, even if the individual regains erectile function, it typically is over a prolonged period, which may take years. During the recovery period, permanent intrapenial damage may occur, leading to some of permanent ED.

Recent advances in the understanding of post-prostatectomy ED pathophysiology have stimulated debate regarding management of this condition, leading to emergence of the concept of penile rehabilitation after prostatectomy. See, e.g., Wang. R., *Penile rehabilitation after radical prostatectomy: where do we stand and where are we going*?, J Sex Med, 2007, 4(4 Pt 2):1085-97; Segal. R. L. et al., *Current penile-rehabilitation strategies: Clinical evidence*. Arab J Urol, 2013, 11(3): 230-6; Gandaglia, G., et al., *Penile rehabilitation after radical prostatectomy: does it work*?, Transl Androl Urol. 2015, 4(2):110-23; Clavell-Hernandez, J. et al, *Penile rehabilitation following prostate cancer treatment: review of current literature*, Asian J Androl. 2015. 17(6):916-22. The rational for such treatment recognizes that prolonged inability to achieve an erection leads to intracorporeal fibrosis, deteriorating penile structures, and progressive worsening of ED, leading to a permanent state of ED.

As discussed in the foregoing literature references, a regular cycle of penile erection is essential for tissue oxygenation and maintenance of penile function in healthy men. Indeed, physiological nocturnal penile tumescence and spontaneous erection during sleep plays a critical role in the maintenance of organ oxygenation and function. Contrarily, prolonged inability to achieve erection leads to chronic penile hypoxia and consequent fibrogenic cytokine production, as described in Gandaglia; Muller, A., et al., *The effect of hyperbaric oxygen therapy on erectile function recovery in a rat cavernous nerve injury model*, J Sex Med. 2008. 5(3): p. 562-70. This unfavorable local intrapenial environment can result in apoptosis and increased collagen production, altering the cavernosal structures. See, e.g., Gandaglia; Moreland. R. B., *Is there a role of hypoxemia in penile fibrosis: a viewpoint presented to the Society for the Study of Impotence*. Int J Impot Res, 1998. 10(2): p. 113-20.

As further discussed in the above literature references, penile rehabilitation is defined as the use of any medical intervention or combination of interventions, at the time of or after prostatectomy, with a goal of increasing penile blood flow and improving intracorporeal oxygenation to avoid or reduce fibrosis until ability to achieve natural erectile function is recovered. The penile rehabilitation treatment preferably should be applied until nerve regeneration is achieved, which may take from between 12-18 months after prostatectomy up to several years. Currently, the state of the art calls for oral PDE5 inhibitors, intracorporeal injection therapy (e.g., Alprostadil), vacuum erection devices, or the combination of these treatments. See, Mulhall, J. P., et al., *Standard operating procedure for the preservation of erectile function outcomes after radical prostatectomy*, J Sex Med. 2013. 10(1):195-203; and Fode, M., et al., *Penile rehabilitation after radical prostatectomy: what the evidence really says*, BJU Int. 2013. 112(7): p. 998-1008. Collectively, clinical trials using these approaches report little or no improvement. See, Clavell-Hernandez; Fode.

On important aspect of diagnosing erectile dysfunction, and monitoring the progress of a penile rehabilitation strategy, is to assess nocturnal penile tumescence ("NPT"). Generally, healthy men between the ages of 18 and 65 have three to five erections per eight hours of sleep. A number of devices have been devised to measure NPT, or which bioelectrical impedance monitoring and the Rigiscan system are the most widely reported in the literature. U.S. Pat. No. 6,015,393 to Hovland et al. describes an apparatus for measuring penile tumescence in which a processor analyzes impedance values sensed from a plurality of sensing elements, such as electrodes, placed on the penis. The bioimpedance described in the patent measures voltage drops between the electrodes to measure variations in the blood flow, which voltage drops may be correlated to penile variable such as length values, cross-sectional values, and volume-filling rates. A drawback inherent in all bioimpedance systems, however, is the inability to adequately calibrate such systems for generalized use across a wide patient population. In addition, such bioimpedance systems can measure dimensional penile changes, but not rigidity.

Similarly, the Rigiscan system, as described for example in U.S. Pat. No. 4,515,166 to Timm, employs a number of loop-like structures that are positioned around the circumference of the penis. Periodically while the patient sleeps, a torque motor and an associated sprocket drive assembly exert a calibration force on the loop-like structures. Displacement of a cable connected to the loops while the torque motor is repetitively activated provides an output function that correlates to the compressibility or rigidity of the penis. Following a series of measurements, two-dimensional or three-dimensional graphic outputs of time versus tumescence can be created. Although still the "gold standard" for measuring NPT, the Rigiscan system includes a number of drawbacks such that it is rarely used. The constricting loops that surround the penis and are periodically tensioned by the motor are generally viewed as intrusive and uncomfortable. Additionally, the monitoring devices is bulky, and may contribute to patient discomfort and potential sleeplessness.

U.S. Pat. No. 9,247,904 to Hotaling describes a device having an adjustable ring forming an opening to position the device at the base of a penis. One or more diagnostic sensors are disposed on an inner surface of the adjustable ring, such that the ring automatically couples the diagnostic sensors to the penis throughout a range of ring diameters. Data generated by the diagnostic sensors is provided to a microcontroller, which outputs data measured during sexual activity. In an alternative embodiment, a replaceable condom-like structure may be coupled to the adjustable ring, and is configured to removably carry one or more longitudinally aligned bend sensors/strain gauges to measure penile axial bending. As will be apparent from the microcontroller housing depicted in the figures of the patent, the bulkiness of the device may interfere with the usefulness and wearability of the device.

In view of the foregoing, there exists a need for systems and methods for use in monitoring penile tumescence to diagnose and treat ED and assist in penile rehabilitation that over the drawbacks of previously known systems. In particular, there exists a need for systems and methods of monitoring penile tumescence that do not interfere with a subject's comfort or sleep patterns.

It further would be desirable to provide methods and apparatus that can continuously measure parameters useful in assessing penile health, including penile length, diameter and rigidity, and which can communicate those measurements to an external device for storage and analysis without bulky electronics.

It still further would be desirable to provide methods and apparatus for monitoring penile tumescence that employs low-cost electronic components, and may be safely worn for one or several intervals when the subject is sleeping.

It is another object of the invention to provide methods and apparatus for monitoring penile tumescence that may be used in conjunction with an implantable electrostimulation array, as described in U.S. Pat. No. 11,141,589, to measure erectile function and reconfigure the electrode array and/or optimize the stimulation parameters employed for electrostimulation for different modes of activation, to enhance erectile function or penile rehabilitation.

SUMMARY OF THE INVENTION

The present invention is directed to tumescence monitoring system for diagnosing erectile dysfunction or facilitating penile rehabilitation, and comprises a condom-like wearable configured to be worn on a subject's penis during sleep intervals and to communicate with a separate controller having a processor. The wearable preferably comprises a flexible latex material and includes a plurality of sensors, such as flexible strain gauges, for monitoring parameters indicative of penile function, including penile circumference, axial extension and rigidity. In an alternative embodiment, the condom-like wearable may employ an electroactive polymer for use in sensing penile rigidity. The controller may be configured to be adhered, e.g., via an adhesive pad, to the subject's groin area and communicate with the wearable via a wire lead. Alternatively, the controller may be configured to be removably affixed to the subject's upper thigh via an elastic strap. The controller may record and store data received from the sensors for later download to a physician's conventional computer, or alternatively may include a wireless transceiver for bi-directional communication with a subject's personal computer or smartphone. The subject's personal computer or smartphone may include software for analyzing and displaying the data.

In an alternative embodiment, the wearable may be configured to wirelessly communicate with the controller. In a preferred embodiment, the wearable may include a plurality of radio frequency identification ("RFID") tags coupled to the plurality of sensors, such that the RFID tags may be wirelessly interrogated by the controller to read the sensor data. In this embodiment, the controller may be configured for placement on the subject's groin area, lower abdomen, and/or upper thigh, or alternatively, may be positioned in close proximity to the subject's bed. In this embodiment also, the controller may be configured to record and store data received from the plurality of sensors on the wearable, or may be configured to retransmit that data to a personal computer or smartphone for review by the subject or the subject's physician.

In accordance with another aspect of the present invention, the tumescence monitoring system of the invention may be used to provide feedback regarding erectile function to an electrostimulation system as described in U.S. Pat. No. 11,141,589 and WO 2022/172157, the entire contents of each of which are incorporated herein by reference. That patent describes an implantable system having an array of electrodes that may be selectively activated after implantation to stimulate an erection. As discussed in that patent, the efficacy of selected electrodes sets in stimulating an erection may be determined either by the physician directing examining the effect of specific electrode configurations, or by measuring the strength of an erection via a sensor. In accordance with one aspect of the present invention, software on a physician's computer that communicates with the controller of the wearable may be configured to interact with the software employed to configure the electrode arrays of the above-mentioned electrostimulation system. In this manner, an erection induced by the electrostimulation system may be directly assessed by the tumescence monitoring system of the present invention. In addition, feedback from the tumescence monitoring system may be used to directly reconfigure the electrode array and/or optimize the stimulation parameters employed by the electrostimulation for different modes of activation, thereby enhancing erectile function and/or penile rehabilitation.

In accordance with one aspect of the present invention, a system for monitoring penile tumescence of a subject is provided. For example, the system may include a wearable comprising a tube of biocompatible flexible and elastic material configured to a disposed on a penis of the subject. The tube may include a plurality of sensors configured to generate data indicative of circumferential and axial dimensional changes of the penis. In addition, the system may include a controller operatively coupled to the plurality of sensors to retrieve and store the data from the plurality of sensors. The controller may be configured to be disposed at a location spaced apart from the penis, and may comprise a transceiver configured to transmit the data to an external computer or smartphone for analysis and display.

At least some of the plurality of sensors may comprise flexible strain gauges. For example, the flexible strain gauges may comprise a capacitive strain gauge comprising an insulated flexible membrane encapsulated by a pair of conductive materials, such that a thickness of the insulated flexible membrane is configured to vary responsive to circumferential and axial dimensional changes of the penis. Accordingly, the controller may be configured to measure capacity of the capacitive strain gauge as the thickness of the insulated flexible membrane varies. Additionally, or alternatively, the flexible strain gauges may comprise an optical strain gauge comprising an optical fiber operatively coupled to a light source and a photodetector configured to measure light intensity. Accordingly, the controller may be configured to: cause the light source to emit a beam of light having a predetermined light intensity through the optical fiber, the beam of light configured to undergo interference as it travels through the optical fiber, the interference configured to vary responsive to strain of the optical fiber due to circumferential and axial dimensional changes of the penis; receive data from the photodetector indicative of a final light intensity of the beam of light measured by the photodetector; and calculate a difference between the predetermined light intensity and the final light intensity of the beam of light, the difference proportional to the strain of the optical fiber.

Moreover, the wearable further may comprise one or more sensors configured to apply a contractile force on the penis during a tumescence event. Accordingly, the controller may be configured to measure penile rigidity based on the contractile force applied to the penis during the tumescence event. For example, the one or more sensors may comprise an electroactive polymer structure configured to apply the contractile force on the penis during the tumescence event. For example, the electroactive polymer structure may comprise a dielectric elastomer actuator comprising alternating layers of an elastomer and one or more electrodes, such that a size and shape of the elastomer may be configured to vary when stimulated by an electric field of the one or more electrodes to thereby apply the contractile force on the penis.

Additionally, or alternatively, the one or more sensors may comprise a wire having a looped end and a free end configured to extend around a circumference of the penis and through the looped end, a spool coupled to the free end of the wire, and a micromotor operatively coupled to the controller and configured to rotate the spool. Accordingly, the controller may be configured to actuate the micromotor to rotate the spool and cause the wire to apply the contractile force on the penis during the tumescence event. Additionally, or alternatively, the one or more sensors may comprise a wire having a looped end and a free end configured to extend around a circumference of the penis and through the looped end, a magnet coupled to the free end of the wire, and an electromagnet assembly operatively coupled to the controller and configured to generate an electromagnetic field. Accordingly, the controller may be configured to actuate the electromagnet assembly to generate the electromagnetic field to move the magnet relative to the electromagnet assembly and cause the wire to apply the contractile force on the penis during the tumescence event. For example, the electromagnet assembly may comprise a single electromagnet, or alternatively, the electromagnet assembly may comprise a series of electromagnets arranged in a linear pattern. In some embodiments, the one or more sensors may comprise a wire comprising a shape memory alloy. e.g., Nitinol, such that a size and shape of the wire may be configured to vary when heated or stimulated by an electric field to apply the contractile force on the penis during the tumescence event. Moreover, a resistivity of the wire may be configured to vary responsive to circumferential and axial dimensional changes of the penis. Accordingly, the controller may be configured to measure the resistivity of the wire.

The controller further may comprise a housing and an adhesive pad coupled to the housing, wherein the adhesive pad is configured to removably secure the controller to a groin area, a lower abdomen, or an upper thigh of the subject. Moreover, the plurality of sensors may be coupled to the controller via a flexible lead. The wearable further may comprise at least one RFID tag, and the controller further may comprise an RFID reader circuit for interrogating the RFID tag. The controller further may comprise a rechargeable battery. In addition, the transceiver may be configured for bi-directional communication with the external computer or the smartphone. Moreover, software installed on the external computer may be configured to provide real-time feedback to physician controller software for selecting electrode configuration or selection of electrostimulation parameters for an implantable array of penile electrostimulation electrodes. The tube may comprise a latex or silicone rubber. In addition, the tube further may comprise a bacteriostatic coating.

In accordance with another aspect of the present invention, a method of monitoring penile tumescence of a subject is provided. The method may include: applying a wearable comprising a tube of biocompatible flexible and elastic material on a penis of the subject, the tube having a plurality of sensors configured to generate data indicative of circumferential and axial dimensional changes of the penis; removably securing a controller to the subject at a location spaced apart from the penis, the controller operatively coupled to the plurality of sensors; operating the controller to retrieve and store data from the plurality of sensors; and transmitting the data to an external computer or smartphone for analysis and display.

Applying the wearable comprising the tube of biocompatible flexible and elastic material on the penis of the subject further may comprise applying a tube having at least some flexible strain gauges. For example, the at least some flexible strain gauges may comprise a capacitive strain gauge comprising an insulated flexible membrane encapsulated by a pair of conductive materials, such that a thickness of the insulated flexible membrane may be configured to vary responsive to circumferential and axial dimensional changes of the penis. Accordingly, the method further may include measuring, by the controller, capacity of the capacitive strain gauge as the thickness of the insulated flexible membrane varies. Additionally, or alternatively, the at least some flexible strain gauges may comprise an optical strain gauge comprising an optical fiber operatively coupled to a light source and a photodetector configured to measure light intensity. Accordingly, the method further may include: causing, by the controller, the light source to emit a beam of light having a predetermined light intensity through the optical fiber, the beam of light configured to undergo interference as it travels through the optical fiber, the interference configured to vary responsive to strain of the optical fiber due to circumferential and axial dimensional changes of the penis; receiving, by the controller, data from the photodetector indicative of a final light intensity of the beam of light measured by the photodetector; and calculating, by the controller, a difference between the predetermined light intensity and the final light intensity of the beam of light, the difference proportional to the strain of the optical fiber.

Removably securing the controller to the subject at the location spaced apart from the penis further may comprise removably securing the controller to a groin area, a lower abdomen, or an upper thigh of the subject using an adhesive pad. The method further may include coupling the plurality of sensors to the controller via a flexible lead. In addition, the method may include applying a contractile force on the penis during a tumescence event to generate data indicative of penile rigidity. For example, the wearable further may comprise an electroactive polymer structure, such that applying the contractile force on the penis during the tumescence event comprises activating the electroactive polymer structure to apply the contractile force on the penis during the tumescence event. Additionally. or alternatively, the wearable further may comprise a dielectric elastomer actuator comprising alternating layers of an elastomer and one or more electrodes, such that applying the contractile force on the penis during the tumescence event comprises actuating the one or more electrodes to generate an electric field to stimulate the elastomer and vary a size and shape of the elastomer to apply the contractile force on the penis during the tumescence event.

Additionally, or alternatively, the wearable further may comprise a wire having a looped end and a free end configured to extend around a circumference of the penis and through the looped end, a spool coupled to the free end of the wire, and a micromotor operatively coupled to the controller and configured to rotate the spool, such that applying the contractile force on the penis during the tumescence event comprises actuating the micromotor to rotate the spool and cause the wire to apply the contractile force on the penis during the tumescence event. Additionally. or alternatively, the wearable further may comprise a wire having a looped end and a free end configured to extend around a circumference of the penis and through the looped end, a magnet coupled to the free end of the wire, and an electromagnet assembly operatively coupled to the controller and configured to generate an electromagnetic field, such that applying the contractile force on the penis during the tumescence event comprises actuating the electromagnet assembly to generate the electromagnetic field to move the magnet relative to the electromagnet assembly and cause the wire to apply the contractile force on the penis during the tumescence event. Additionally, or alternatively, the wearable further may comprise a wire comprising a shape memory alloy, such that applying the contractile force on the penis during the tumescence event comprises heating or electrically stimulating the wire to vary a size and shape of the wire to apply the contractile force on the penis during the tumescence event. Moreover, the method further may include measuring a resistivity of the wire as the wire deforms responsive to circumferential and axial dimensional changes of the penis.

The wearable further may comprise at least one RFID tag, such that the method further may include operating the controller to retrieve and store data from the plurality of sensors by retrieving data from the plurality of sensors using an RFID reader circuit for interrogating the at least one RFID tag. In addition, the method may include transmitting programmed instructions from the external computer or smartphone to the controller. Moreover, the method further may include using the wearable and controller to record data indicating nocturnal tumescence events. The external computer further may be configured to select at least one of electrode configuration or electrostimulation parameters for an implantable array of penile electrostimulation electrodes, such that the method further may include using the wearable and controller to provide real-time feedback to assist in selecting at least one of electrode configuration or electrostimulation parameters for the implantable array of penile electrostimulation electrodes.

Other features of the inventive system and methods will be apparent with reference to the following description and figures.

DETAILED DESCRIPTION OF THE INVENTION

The present invention is a system and methods for monitoring penile tumescence that overcome the disadvantages of prior art systems, and in particular, discomfort caused previously known systems and methods. The tumescence monitoring system of described herein is expected to provide accurate results with less inconvenience to the wearer, and especially when used to monitoring nocturnal penile tumescence. In addition, the system may be used in conjunction with the implantable electrostimulation system described in above-incorporated U.S. Pat. No. 11,141,589 to assess the strength of an erection stimulated by specific electrode configurations and stimulation parameters, to enable optimization of the electrode configuration and electrostimulation parameters.

Figure 1:
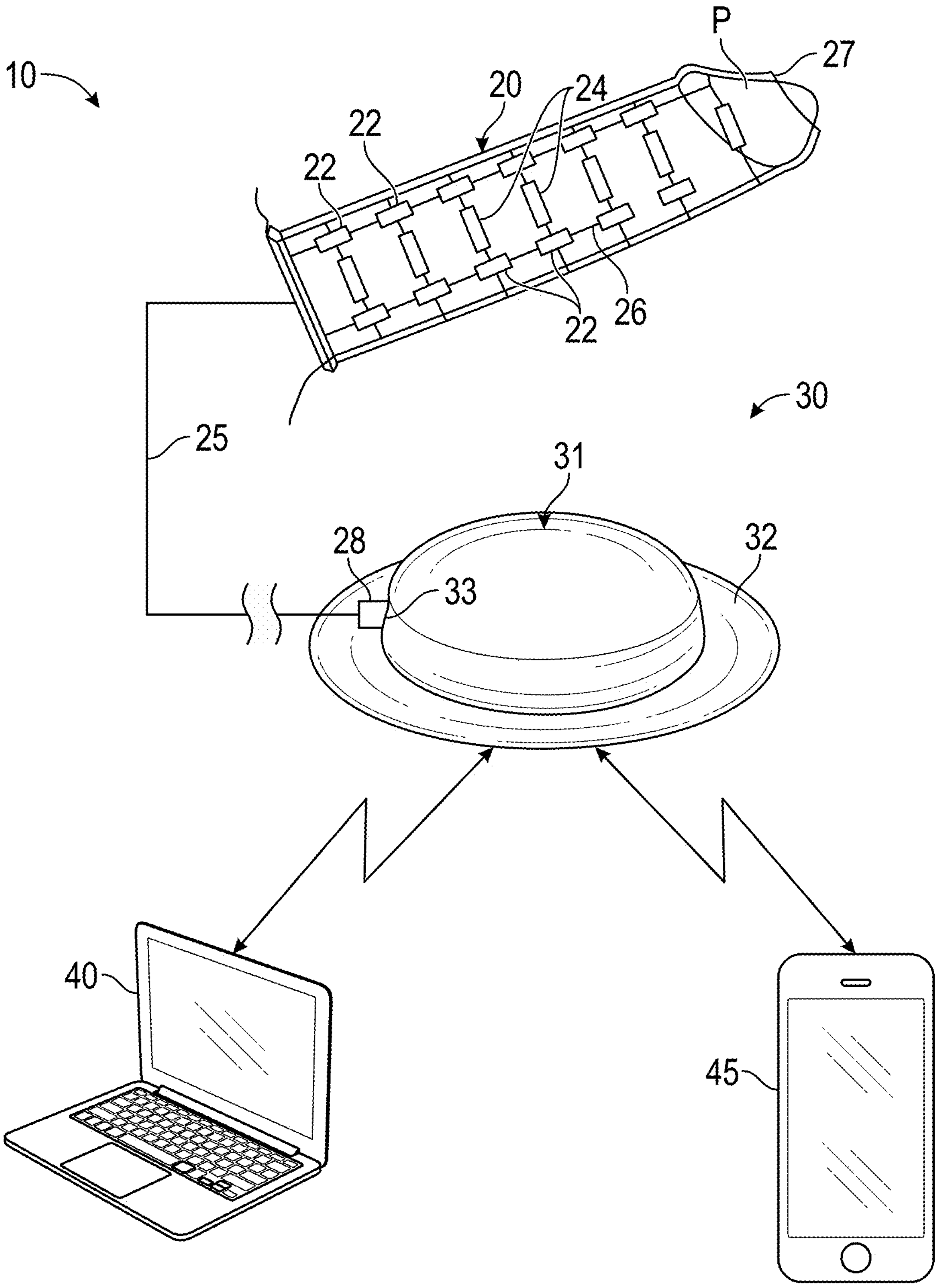
FIG. 1 is a schematic diagram of an exemplary system arranged in accordance with the principles of the present invention for use in monitoring penile tumescence.
Figure 2:
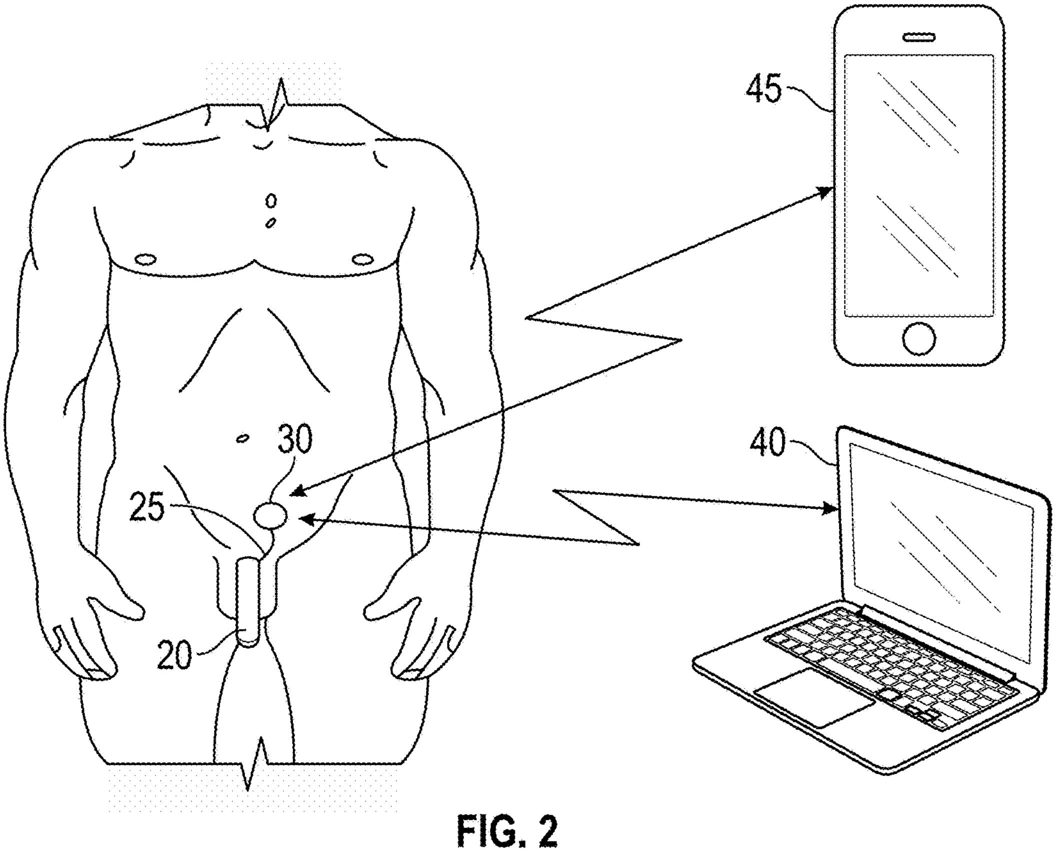
FIG. 2 is a schematic view depicting exemplary placement of the components of the system of FIG. 1 in use with a subject.

Referring to FIGS. 1 and 2, exemplary system 10 of the present invention is described. In FIG. 1, components of the system are not depicted to scale on either a relative or absolute basis. System 10 comprises condom-like wearable 20 coupled via flexible lead 25 to controller 30, which in turn wirelessly communicates with personal computer 40 and/or smartphone 45. As best shown in FIG. 2, wearable 20 is disposed on the penis of the subject, and controller 30 may be adhered via a biocompatible adhesive pad to the subject's groin area, lower abdomen, and/or upper thigh, and coupled to wearable 20 via flexible lead 25. When so arranged, controller 30 may communicate data to personal computer 40 and/or smartphone 45 via a known wireless technology, such as WiFi or Bluetooth.

Referring still to FIG. 1, wearable 20 preferably comprises a biocompatible elastic material, such as latex or silicone rubber, and includes a plurality of flexible sensors 22, 24 mounted thereon, or embedded within its thickness, for example, strain gauges, which are configured to measure changes in the circumference of the subject's penis, as well as axial extension thereof. Sensors 22 and 24 may be of different types, as best suited for measuring circumferential or axial strains, and generally may be of the type of flexible strain gauges described by C. Zhao et al, in the article entitled "3D-printed highly stable flexible strain sensor based on silver-coated-glass fiber-filled conductive silicone rubber." Materials and Design 193 (2020) 108788, https://doi.org/10.1016/j.matdes.2020.108788.

Additionally, or alternatively, sensors 22 and 24 may be of the type of flexible capacitive strain gauges described by H. Souri et al, in the article entitled "Wearable and Stretchable Strain Sensors: Materials, Sensing Mechanisms, and Applications," Advanced Intelligent Systems (2020) 2000039, https://doi.org/10.1002/aisy.202000039. For example, each flexible capacitive strain gauge may include an insulated flexible membrane encapsulated by a pair of conductive materials, e.g., a dielectric, such that upon deformation, the thickness of the insulated flexible membrane varies based on the degree of deformation. Accordingly, the capacity of the flexible capacitive strain gauge may be measured, which is indicative of the tumescence of the subject's penis.

Additionally, or alternatively, sensors 22 and 24 may be of the type of flexible optical strain gauges described by J. Guo et al. in the article entitled "Highly Flexible and Stretchable Optical Strain Sensing for Human Motion Detection," Optica 4, 1285-1288 (2017), https://doi.org/10.1364/OPTICA.4.001285, or by J. Jeong et al. in the article entitled "Highly Stretchable Polymer-based Optical Strain Sensor for Integration with Soft Actuator," 2019 IEEE International Conference on Consumer Electronics (ICCE), Las Vegas, NV, USA, 2019. pp. 1-3, doi: 10.1109/ICCE.2019.8661937, https://iecexplore.ieec.org/document/8661937. For example, each flexible optical strain gauge may include an optical fiber operatively coupled to a light source and a photodetector configured to measure the intensity of a beam of light through the optical fiber. Accordingly, the light source may send a beam of light through the optical fiber, which undergoes interference due to changes in the optical fiber's optical properties caused by strain on the optical fiber. The power difference between the light source and the photodetector is proportionate to the strain, and thus indicative of the tumescence of the subject's penis.

Sensors 22 and 24 may be coupled to grid 26 of elastic conductors disposed on or embedded in the wearable to permit the sensors to be individually read by controller 30 via flexible lead 25. As will be understood, wearable 20 is elastic and has sufficiently low durometer to be capable of undergoing circumference and axial expansion and contraction to mimic the degree of flaccidness or tumescence of penis P of the subject.

Wearable 20 is designed to be worn by the subject while sleeping to continuously monitor the state of the penis, and may include aperture 27 at its distal end to permit the subject to get up to urinate during the night without removing wearable 20. Flexible lead 25 may comprise a wire lead or flexible ribbon, and preferably has a length. e.g., 25-40 cm, sufficient to permit connector 28 of lead 25 to be connected to controller 30 when the controller is adhered to the subject's groin area, lower abdomen, and/or upper thigh. Wearable 20 may include a bacteriostatic coating to permit the wearable to be worn on a number of successive nights to collect tumescence data, e.g., three consecutive nights, before being discarded. Alternatively, wearable 20 may be designed for use for a single night and replaced with a fresh wearable on subsequent nights for which data is to be acquired.

In one embodiment, controller 30 comprises plastic housing 31 that contains a printed circuit board having electronics for reading the sensors on wearable 20. Controller 30 may be removably fastened to a biocompatible adhesive patch 32, which permits the controller to be removably attached to the subject's groin area, lower abdomen, and/or upper thigh. Adhesive patch 32 may have biocompatible adhesive on both sides to permit the patch to be replaced daily. As depicted in FIG. 1, housing 31 of controller 30 preferably has a dome-like form, to minimize abrupt edges that may snag on the subject's clothing or sleepwear. In addition, controller 30 has port 33 for accepting connector 28 of wearable 20.

Figure 3:
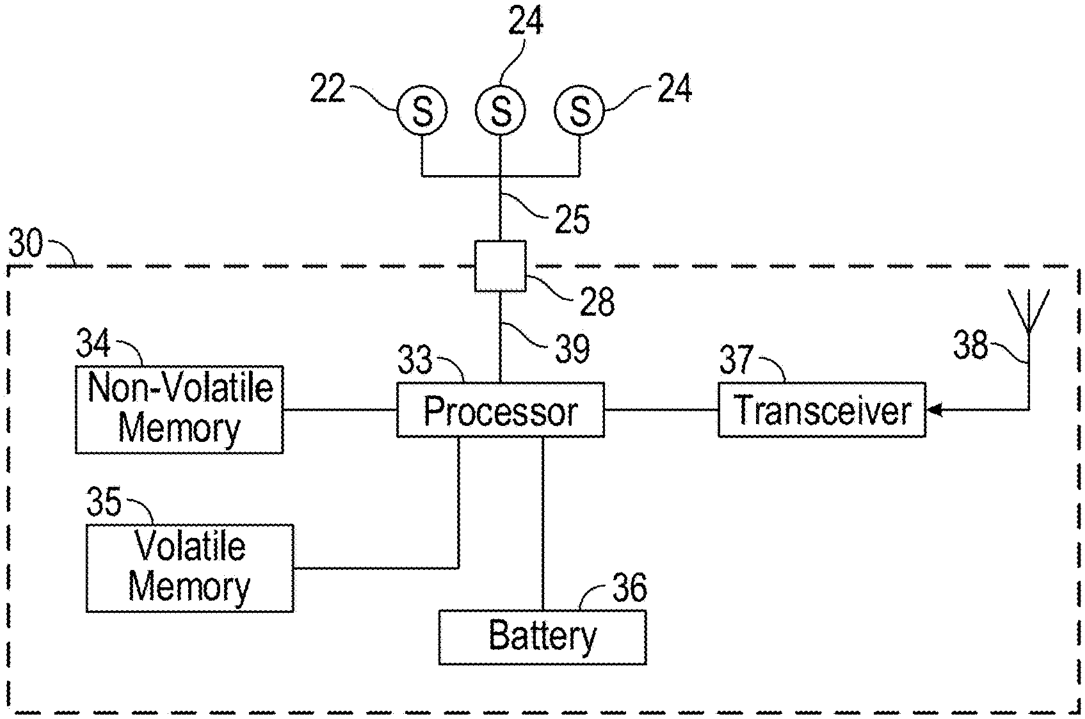
FIG. 3 is a schematic diagram of the internal components of a first embodiment of the controller of the present invention.

Referring now to FIG. 3, the electronic components of controller 30 are described. In particular, controller 30 includes processor 33, non-volatile memory 34, volatile memory 35, battery 36, transceiver 37, antenna 38, and bus 39. Bus 39 couples the internal components 33-38 of the controller, and includes a port for accepting connector 28 of flexible lead 25, thereby coupling sensors 22, 24 to controller 30. Processor 33 may be a general purpose processor capable of reading programmed instructions stored in non-volatile memory 34 to read and analyze the signals generated by sensors 22, 24 to generate tumescence data using volatile memory 35. The programmed instructions also may store the tumescence data in storage locations of non-volatile memory 34, and subsequently transfer that data to personal computer 40 and/or smartphone 45 using transceiver 37 and antenna 38. Alternatively, processor 33 may be a special purpose built processor for handling collection and analysis of the data received from wearable 20. Battery 36 may be a lithium ion battery with sufficient capacity to support operation of processor 33, reading of sensors 22 and 24, and support operation of transceiver 37 for a desired period, such as 3 to 5 days. When controller 30 is not in use by a subject, battery 36 may be recharged, e.g., using a conventional charging circuit and jack (not shown).

Transceiver 37 and antenna 38 preferably are configured for bi-directional communication with personal computer 40 and/or smartphone 45 to transfer tumescence data from controller 30 to computer 40 and/or smartphone 45, and also to update the programmed instructions stored in non-volatile memory 34. Transceiver 37 may be compliant with any of a number of well-known wireless standards, such as IEEE 802.11 for WiFi or Bluetooth standard, IEEE 802.15.1 or as currently promulgated by the Bluetooth Special Interest Group.

Personal computer 40 may belong either to the subject whose erectile function is being evaluated or the subject's physician, while smartphone 45 preferably belongs to the subject. In one preferred embodiment, personal computer 40 may be programmed with software for bi-directionally communicating with controller 30 to retrieve tumescence data stored in non-volatile memory 34, or to update the programmed instructions stored in non-volatile memory 34 for processor 33. Computer 40 and/or smartphone 45, in addition, may contain additional software for analyzing and displaying the tumescence data, for example, to show nocturnal erection events, including circumferential and length changes.

In accordance with one aspect of the present invention, computer 40 also may contain the software for external physician controller 500 for programming configuration of the electrode array and electrostimulation parameters used by the implantable electrode array described with respect to FIGS. 1 and 7, and in column 12, lines 10-64 of U.S. Pat. No. 11,141,589. In this case, the software of the tumescence monitoring system in computer 40 may directly interact with the software for external physician controller 500 to directly measure the erectile response to a selected electrode configuration and/or set of electrostimulation parameters. Accordingly, the tumescence monitoring system of the present invention may be used to interact with, and thus optimize, the erectile response achievable for the implantable electrode array, as desired to achieve a desired erectile response or response for penile rehabilitation.

Still referring to FIGS. 1 to 3, an alternative embodiment of wearable 20 may comprise an electroactive polymer, such as a dielectric elastomer, for measuring penile rigidity during tumescence events. In this case, sensors 22 may instead comprise electroactive polymer structures embedded within the wall of wearable 20 and be coupled via flexible lead 25 to a voltage source. i.e., battery, in controller 30. Upon application of a voltage, the electroactive polymer may contract, as described for example in U.S. Pat. No. 7,862,551 to Bates. Additionally. or alternatively, the electroactive polymer may be of the type of dielectric elastomer actuator (DEA) described by S. Perrin, in the article entitled "A Tiny Pump Comes to the Aid of Weakened Hearts" (available at: https://actu.epfl.ch/news/a-tiny-pump-comes-to-the-aid-of-weakened-hearts/), or by T. Martinez, in the article entitled "A Novel Soft Cardiac Assist Device based on a Dielectric Elastomer Augmented Aorta: An In Vivo Study" (2022), https://doi.org/10.1002/btm2.10396. For example, the DEA may include a plurality of alternating layers of elastomer and electrodes that are joined together, such that the elastomer exhibits a change in size or shape when stimulated by an electrical field applied by the electrodes. Accordingly, the change exhibited by the elastomer layers may be measured, which is indicative of penile rigidity. Additionally, or alternatively, sensors 22 may instead comprises other actuator types for measuring penile rigidity, as described in further detail below.

As employed in wearable 20 of the present invention, during nocturnal monitoring with system 10, when a change in penile circumference is detected by sensors 24 (e.g. more than a 5 mm increase), controller 30 may deliver an electric field to induce a short controlled contraction of the electroactive polymer structures and/or DEA. Based on the force of the contraction imposed by the electroactive polymer structures and the resulting change in circumference detected by sensors 24, instantaneous stiffness/rigidity of the penis may be calculated by controller 30. When the penile circumference returns to a baseline value, application of voltage by the controller to the electroactive polymer structures is discontinued. Preferably such measurements may be repeated every 10 to 20 minutes beginning shortly after a change in penile circumference is detected during an erection event, and the cycle repeated for every subsequent erectile event.

Figure 4:
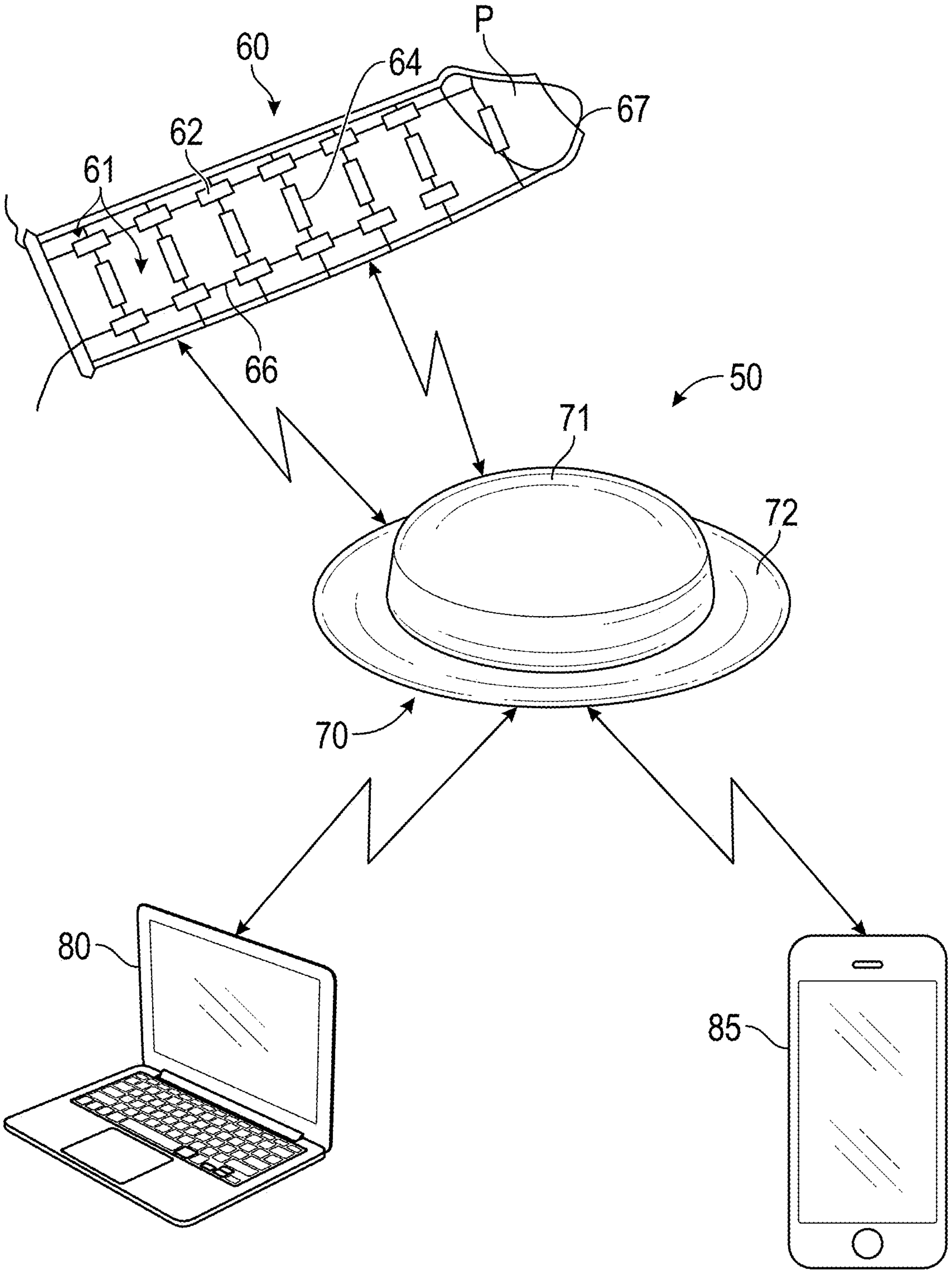
FIG. 4 is a schematic diagram of the electronic components of an exemplary embodiment of the implantable device.
Figure 5:
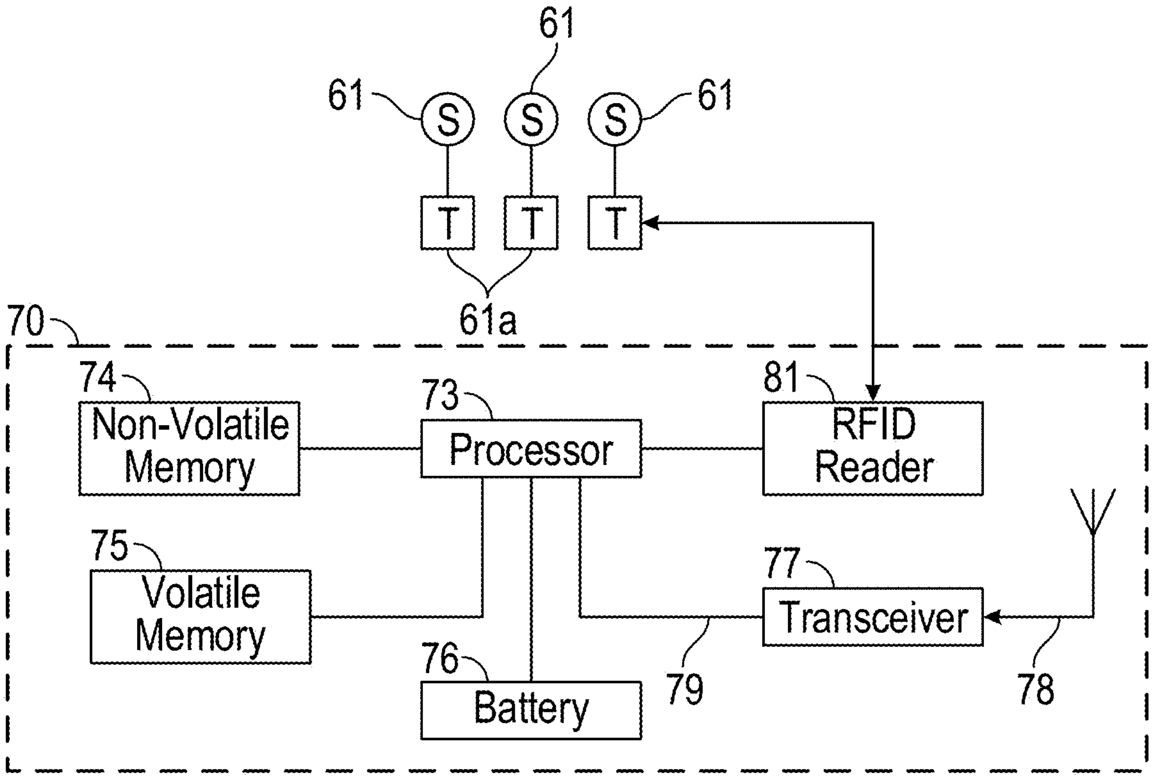
FIG. 5 is schematic diagram of the internal components of an alternative embodiment of the controller of the present invention.

Referring now to FIGS. 4 and 5, a further alternative embodiment of penile tumescence monitoring system 50 of the present invention is described. In FIG. 4, components of the system again are not depicted to scale on either a relative or absolute basis. System 50 is similar to the embodiments of system 10 described with respect to FIGS. 1-3, except that in system 50 the sensors disposed on or within wearable 60 wirelessly communicate with controller 70. Controller 70 in turn wirelessly communicates with personal computer 80 and/or smartphone 85, as in the earlier embodiment. System 50 is configured so that, similarly to FIG. 2, wearable 60 is disposed on the penis of the subject, while controller 70 may be adhered via a biocompatible adhesive pad to the subject's groin area or lower abdomen, removably secured to the subject's upper thigh using an elastic or Velcro® strap, or even placed on a nightstand near the subject's bed. Wearable 60 wirelessly transmits data to controller 70, and thus omits the need for a flexible lead, further reducing subject discomfort. Controller 70 may communicate data to personal computer 80 and/or smartphone 85 via a known wireless technology, such as WiFi or Bluetooth.

Referring still to FIG. 4, wearable 60 preferably comprises a biocompatible elastic material, such as latex or silicone rubber, and has plurality of sensors 61 mounted thereon, or embedded within its thickness. Sensors 61 may be flexible strain gauges, 62 and 64, such as described in the above identified articles, and may be of the same type, but oriented differently on wearable 60 to measure circumferential and length changes of the subject's penis. Alternatively, strain gauges 62 and 64 may be of different types as best suited for measuring circumferential or axial strains. As a further alternative embodiment, wearable 60 also may comprise electroactive polymer structures, as described in the preceding embodiment. As a yet further alternative embodiment, some of sensors 61 may comprise flexible bands that have circumferentially overlapping portions that serve as rheostats, so that a resistance value generated by the band changes as a function of its circumferential or axial extension. Additionally, or alternatively, sensors 61 may be of the type of a wire band formed of a shape memory alloy, e.g., Nitinol, that may return to its original shape when heated above its transformation temperature or exposed to an electrical current, as described in the article entitled "Smart Grippers Powered by Shape Memory Alloys" (available at: https://www.epfl.ch/labs/lai/research/page-101809-en-html/page-153681-en-html/). The wire band may be permanently deformed to a desired shape and size by being heated above its shape-setting temperature. e.g., 400° C.-550° C., and then cooled down while maintaining the desired shape and size. Moreover, upon deformation, the resistivity of the Nitinol wire band will vary based on the degree of deformation. Accordingly, the resistance value of the wire band may be measured, which is indicative of penile rigidity.

In accordance with once aspect of the invention, sensors 61 may each include an RFID tag that periodically is wirelessly interrogated by controller 70 to generate a value corresponding to penile axial or circumferential dimensional changes, or which permit the calculation of penile rigidity. Such RFID-enabled strain gauges are described, for example, in U.S. Pat. No. 9,464,948 to Carroll et al., which is incorporated herein by reference. For example, each of sensors 61 may be interrogated by controller 70 every second or even more frequently to provide a nearly continuous stream of data indicative of the tumescence of penis P.

Alternatively, sensors 61 of wearable 60 may be coupled to grid 66 of elastic conductors disposed on or embedded in the wearable, such that a common RFID tag may be employed by controller 70 to individually read sensors 61. As will be understood, wearable 60 is elastic and has sufficiently low durometer to undergo circumference and axial expansion and contraction to mimic the degree of flaccidness or tumescence of penis P of the subject.

Wearable 60 also is designed to be worn by the subject while sleeping to continuously monitor the state of the penis, and may include aperture 67 at its distal end to permit the subject to get up to urinate during the night without removing the wearable. Wearable 60 may include a bacteriostatic coating to permit the wearable to be worn on a number of successive nights to collect tumescence data, e.g., three consecutive nights, before being discarded. Alternatively, wearable 60 may be designed for use for a single night and replaced with a fresh wearable on subsequent nights for which data is to be acquired.

In the embodiment of FIGS. 4 and 5, controller 70 comprises plastic housing 71 that contains a printed circuit board having electronics for wirelessly reading the sensors on wearable 60, and storing and communicating such data to computer 80 and/or smartphone 85. As discussed above, controller 70 may be removably fastened to the subject's groin or lower abdomen using biocompatible adhesive patch 72, strapped to the subject's upper thigh using a strap (not shown), or placed on a table or nightstand in close proximity to the subject's bed. Adhesive patch 72 may have biocompatible adhesive on both sides to permit the patch to be replaced daily. As for the preceding embodiment, housing 71 of controller 70 preferably has a smooth dome-like form to minimize edges that could snag on the subject's clothing or sleepwear.

Referring to FIG. 5, the electronic components of controller 70 are described. Controller 70 includes processor 73, non-volatile memory 74, volatile memory 75, battery 76, transceiver 77, antenna 78, internal bus 79, and RFID reader circuit 81. In FIG. 5, each of sensors 61 is depicted having an associated RFID tag 61*a*, to permit sensors 61 to be individually read by controller 70. Processor 73 may be a general purpose processor capable of reading programmed instructions stored in non-volatile memory 74 to read and analyze the signals generated by sensors 62, 64 to generate tumescence data using volatile memory 75. The programmed instructions also may store the tumescence data in storage locations of non-volatile memory 74, and subsequently transfer that data to personal computer 80 and/or smartphone 85 using transceiver 77 and antenna 78. Alternatively, processor 73 may be a special purpose built processor for handling collection and analysis of the data received from wearable 60. Battery 76 may be a lithium ion battery with sufficient capacity to support operation of processor 73, reading of sensors 62 and 64 via RFID reader circuit 81, and to support operation of transceiver 77 for a desired period, such as 1 to 5 days. Battery 76 also should be capable of storing sufficient energy to energize the electroactive polymer structures in wearable 60, if present, for evaluating penile rigidity. When controller 70 is not in use by a subject, battery 76 may be recharged, e.g., using a conventional charging circuit and jack (not shown), Transceiver 77 and antenna 78 preferably are configured for bi-directional communication with personal computer 80 or smartphone 85 to transfer tumescence data from controller 70 to computer 80 and/or smartphone 85, and also to update the programmed instructions stored in non-volatile memory 74. Transceiver 77 may be compliant with any of a number of well-known wireless standards, such as IEEE 802.11 for WiFi or Bluetooth standard, IEEE 802.15.1 or as currently promulgated by the Bluetooth Special Interest Group.

RFID tags 61*a* preferably are passive, and are read by collecting radio-frequency energy emitted by RFID reader 81, using the principle of operation as described in the above-incorporated U.S. Pat. No. 9,464,948. Data retrieved from sensors 61 by RFID reader circuit 81 is processed by processor 73 and stored in non-volatile memory 74 for subsequent transmission and analysis by computer 80 and/or smartphone 85.

As in the preceding embodiment of system 10, personal computer 80 of system 50 may belong either to the subject whose erectile function is being evaluated or the subject's physician, while smartphone 85 preferably may belong to the subject. Personal computer 80 preferably is programmed with software for bi-directionally communicating with controller 70 to retrieve tumescence data stored in non-volatile memory 74, and to update the programmed instructions stored in non-volatile memory 74 that are used by processor 73. Computer 80 or smartphone 85, in addition, may contain additional software for analyzing and displaying the tumescence data, for example, to show real-time erection events or previously recorded nocturnal erection events, including circumferential and length changes and rigidity values.

As for the preceding embodiment, computer 80 also may contain the software for external physician controller 500 for programming configuration of the electrode array and electrostimulation parameters used by the implantable electrode array described with respect to FIGS. 1 and 7, and in column 12, lines 10-64 of U.S. Pat. No. 11,141,589. In this case, the software of the tumescence monitoring system in computer 80 may directly interact with the software for external physician controller 500, under the control of the subject's physician or automatically, to measure the erectile response to a selected electrode configuration and/or set of electrostimulation parameters. In this manner, the tumescence monitoring system of the present invention may be used to provide near real-time data to external physician controller 500 used to configure operation of the implantable electrode array, thus optimizing the erectile response attained by the implantable electrode array, to achieve a desired erectile response or penile rehabilitation regime.

Alternative systems for measuring penile rigidity are described. The system may include a wire connected to a spool configured to be activated by a micromotor, e.g., a coreless DC brushed micromotor. The wire may be positioned around the circumference of the subject's penis. For example, the wire may have a looped end opposite to a free end of the wire, such that the free end of the wire may extend around the circumference of the subject's penis and through the looped end, and connected to the spool. Moreover, a micromotor may be programmed to actuate the spool to rotate and wind the wire, thereby applying a force to the wire around the penis. Displacement of the wire responsive to actuation of the micromotor provides an output function that correlates to the compressibility or rigidity of the penis. Unlike the RigiScan system, the single small wire and the micromotor are less intrusive and less uncomfortable to the subject. e.g., during sleep.

The system may include a wire connected to a ferromagnetic or conductive material. e.g., a magnet, which may be attracted by an electromagnet assembly. The wire may be positioned around the circumference of the subject's penis. For example, the wire may have a looped end opposite to a free end of the wire, such that the free end of the wire may extend around the circumference of the subject's penis and through the looped end, and connected to a magnet. The electromagnetic assembly may comprise a single electromagnet, or alternatively, a series of electromagnets arranged in a linear pattern forming a linear actuator. Accordingly, the electromagnetic assembly may be programmed to be actuated to emit an electromagnet field, which causes movement of the magnet relative to the electromagnetic assembly, thereby applying a force to the wire around the penis. Displacement of the wire responsive to actuation of the electromagnetic assembly provides an output function that correlates to the compressibility or rigidity of the penis.

While various illustrative embodiments of the invention are described above, it will be apparent to one skilled in the art that various changes and modifications may be made therein without departing from the invention.

What is claimed is:

1. A system for monitoring penile tumescence of a subject, the system comprising:

a wearable comprising:

a tube of biocompatible flexible and elastic material configured to be disposed on a penis of the subject, the tube having a plurality of sensors configured to generate data indicative of circumferential and axial dimensional changes of the penis; and at least one sensor configured to apply a contractile force on the penis during a tumescence event, the at least one sensor comprising a wire comprising a shape memory alloy, a size and shape of the wire configured to vary when heated or stimulated by an electric field to apply the contractile force on the penis during the tumescence event; and a controller operatively coupled to the plurality of sensors and the at least one sensor, the controller configured to be disposed at a location spaced apart from the penis, the controller comprising a transceiver and instructions that, when executed by one or more processors of the controller, cause the controller to:

retrieve and store the data from the plurality of sensors;

transmit, via the transceiver, the data to an external computer or smartphone for analysis and display; and measure penile rigidity based on the contractile force applied to the penis during the tumescence event.

2. The system of claim 1, wherein at least one sensor of the plurality of sensors comprises a flexible strain gauge.

3. The system of claim 2, wherein the flexible strain gauge comprises a capacitive strain gauge comprising an insulated flexible membrane encapsulated by a pair of conductive materials, a thickness of the insulated flexible membrane configured to vary responsive to circumferential and axial dimensional changes of the penis, and wherein the controller is configured to measure capacity of the capacitive strain gauge as the thickness of the insulated flexible membrane varies.

4. The system of claim 2, wherein the flexible strain gauge comprises an optical strain gauge comprising an optical fiber operatively coupled to a light source and a photodetector configured to measure light intensity, and wherein the controller is configured to:

cause the light source to emit a beam of light having a predetermined light intensity through the optical fiber, the beam of light configured to undergo interference as it travels through the optical fiber, the interference configured to vary responsive to strain of the optical fiber due to circumferential and axial dimensional changes of the penis;

receive data from the photodetector indicative of a final light intensity of the beam of light measured by the photodetector; and calculate a difference between the predetermined light intensity and the final light intensity of the beam of light, the difference proportional to the strain of the optical fiber.

5. The system of claim 1, wherein a resistivity of the wire is configured to vary responsive to circumferential and axial dimensional changes of the penis, and wherein the controller is configured to measure the resistivity of the wire.

6. The system of claim 1, wherein the wire comprises Nitinol.

7. The system of claim 1, wherein the controller further comprises a housing and an adhesive pad coupled to the housing, wherein the adhesive pad is configured to removably secure the controller to a groin area, a lower abdomen, or an upper thigh of the subject.

8. The system of claim 7, wherein the plurality of sensors is coupled to the controller via a flexible lead.

9. The system of claim 1, wherein the wearable further comprises at least one RFID tag.

10. The system of claim 9, wherein the controller further comprises an RFID reader circuit for interrogating the RFID tag.

11. The system of claim 1, wherein the controller further comprises a rechargeable battery.

12. The system of claim 1, wherein the transceiver is configured for bi-directional communication with the external computer or the smartphone.

13. The system of claim 1, further comprising software configured to be installed on the external computer, the software configured to be executed by one or more processors of the external computer to cause the external computer to provide real-time feedback to physician controller software for selecting electrode configuration or selection of electrostimulation parameters for an implantable array of penile electrostimulation electrodes.

14. The system of claim 1, wherein the tube comprises a latex or silicone rubber.

15. The system of claim 1, wherein the tube further comprises a bacteriostatic coating.

16. A system for monitoring penile tumescence of a subject, the system comprising:

a wearable comprising a tube of biocompatible flexible and elastic material configured to be disposed on a penis of the subject, the tube having a plurality of sensors configured to generate data indicative of circumferential and axial dimensional changes of the penis;

at least one sensor configured to apply a contractile force on the penis during a tumescence event, the at least one sensor comprising:

a wire having a looped end and a free end configured to extend around a circumference of the penis and through the looped end;

a spool coupled to the free end of the wire; and a micromotor configured to rotate the spool; and a controller operatively coupled to the plurality of sensors, the at least one sensor, and the micromotor, the controller configured to be disposed at a location spaced apart from the penis, the controller comprising a transceiver and instructions that, when executed by one or more processors of the controller, cause the controller to:

retrieve and store the data from the plurality of sensors;

transmit the data to an external computer or smartphone for analysis and display:

actuate the micromotor to rotate the spool and cause the wire to apply the contractile force on the penis during the tumescence event; and measure penile rigidity based on the contractile force applied to the penis during the tumescence event.

17. A method of monitoring penile tumescence of a subject, the method comprising:

applying a wearable comprising a tube of biocompatible flexible and elastic material on a penis of the subject, the tube having a plurality of sensors configured to generate data indicative of circumferential and axial dimensional changes of the penis;

removably securing a controller to the subject at a location spaced apart from the penis, the controller operatively coupled to the plurality of sensors;

operating the controller to retrieve and store data from the plurality of sensors;

transmitting the data to an external computer or smartphone for analysis and display;

applying, via a wire comprising a shape memory alloy, a contractile force on the penis during a tumescence event by heating or stimulating by an electric field the wire to vary a size and shape of the wire during the tumescence event; and measuring penile rigidity based on the contractile force applied to the penis during the tumescence event.

18. The method of claim 17, wherein a resistivity of the wire is configured to vary responsive to circumferential and axial dimensional changes of the penis, the method further comprising measuring the resistivity of the wire as the wire deforms responsive to circumferential and axial dimensional changes of the penis.

* * * * *